US012604121B2

(12) United States Patent
Fricker et al.

(10) Patent No.: US 12,604,121 B2
(45) Date of Patent: Apr. 14, 2026

(54) MONITORING ENVIRONMENTAL CONDITIONS OF STORAGE UNITS FOR VACCINES AND OTHER CLIMATE SENSITIVE PRODUCTS

(71) Applicant: Copeland Cold Chain LP, Kennesaw, GA (US)

(72) Inventors: Scott N. Fricker, Shakopee, MN (US); Niles E. Falasco, Myrtle Beach, SC (US); Ethan M. Hansen, Eden Prairie, MN (US); David G. Lehtola, Aitkin, MN (US)

(73) Assignee: Copeland Cold Chain LP, Kennesaw, GA (US)

( * ) Notice: Subject to any disclaimer, the term of this patent is extended or adjusted under 35 U.S.C. 154(b) by 69 days.

(21) Appl. No.: 18/755,080

(22) Filed: Jun. 26, 2024

(65) Prior Publication Data

US 2025/0008245 A1 Jan. 2, 2025

Related U.S. Application Data

(60) Provisional application No. 63/523,835, filed on Jun. 28, 2023.

(51) Int. Cl.
*H04Q 9/02* (2006.01)
*G16H 40/67* (2018.01)

(52) U.S. Cl.
CPC ............... *H04Q 9/02* (2013.01); *G16H 40/67* (2018.01); *H04Q 2209/40* (2013.01)

(58) Field of Classification Search
CPC ....... H04Q 9/02; H04Q 2209/40; G16H 40/67
(Continued)

(56) References Cited

U.S. PATENT DOCUMENTS 8,271,197 B2 9/2012 Fogarty et al.
9,092,967 B2 7/2015 Schechter
(Continued)

FOREIGN PATENT DOCUMENTS

WO WO-2020008207 A1 1/2020

OTHER PUBLICATIONS

PCT International Search Report and Written Opinion for PCT/US2024/035552 that is the parent application to the instant application; dated Oct. 14, 2024; 15 pages.
(Continued)

*Primary Examiner* — Omar Casillashernandez
(74) *Attorney, Agent, or Firm* — Harness, Dickey & Pierce, P.L.C.; Anthony G. Fussner

(57) ABSTRACT

Disclosed are exemplary embodiments of environmental monitoring devices for monitoring one or more environmental conditions (e.g., temperature, humidity, carbon dioxide, oxygen, pressure, etc.) of storage units, such as storage units for vaccines, medications, and other climate sensitive products, etc. Also disclosed are exemplary methods of selectively configuring an environmental monitoring device for wireless communication by selectively connecting a communication module, from a plurality of different wireless communication modules, with an expansion port/connector of a printed circuit board of the environmental monitoring device. Further disclosed are exemplary methods of copying a configuration of a first environmental monitoring device to at least one or more other more environmental monitoring devices over a wireless communication link.

26 Claims, 19 Drawing Sheets

1. The device will have a module design so that the "C" board can be swapped depending on the communication method required by the end user - Wi-Fi, cellular, 900 MHz, etc.

2. A single configured device will also be able to wirelessly configure multiple devices via BLUETOOTH communication.

A | Main Platform board (+BLE)
Can be repackaged in smaller form factor

B | Display Board

C | Expansion board
Can accommodate Wi-Fi/ 900MHz / Cellular

(58) Field of Classification Search
USPC .................................................. 340/539.22
See application file for complete search history.

(56) References Cited

U.S. PATENT DOCUMENTS

| | | | |
|---|---|---|---|
| 9,247,322 | B1 | 1/2016 | Schechter et al. |
| 9,332,322 | B2 | 5/2016 | Niemeyer et al. |
| 9,541,454 | B2 | 1/2017 | Schechter et al. |
| 9,857,233 | B2 | 1/2018 | Schechter et al. |
| 9,877,089 | B2 | 1/2018 | Branch et al. |
| 10,209,688 | B2 | 2/2019 | Stefanski et al. |
| 10,475,046 | B2 | 11/2019 | Schechter |
| 10,704,960 | B2 | 7/2020 | Schechter et al. |
| 2011/0028093 | A1 | 2/2011 | Patel et al. |
| 2013/0087628 | A1* | 4/2013 | Nelson ............... G05D 23/1934 |
| | | | 236/51 |
| 2013/0311140 | A1 | 11/2013 | Schechter |
| 2015/0106447 | A1 | 4/2015 | Hague |
| 2015/0276266 | A1* | 10/2015 | Warren ................... H04W 4/70 |
| | | | 700/300 |
| 2015/0289768 | A1* | 10/2015 | Toriumi ................. A61B 5/746 |
| | | | 340/588 |
| 2016/0061476 | A1 | 3/2016 | Schultz et al. |
| 2016/0161138 | A1* | 6/2016 | Fadell .................... G06Q 50/06 |
| | | | 700/278 |
| 2018/0132183 | A1* | 5/2018 | Gattu ............... H04W 52/0203 |
| 2018/0220514 | A1 | 8/2018 | Harris |
| 2018/0277255 | A1 | 9/2018 | Martin et al. |
| 2019/0219294 | A1* | 7/2019 | Dutt ................... G05B 19/0421 |
| 2021/0289768 | A1 | 9/2021 | Plank et al. |

OTHER PUBLICATIONS

TempTrak® Wi-Fi (802.11 b/g/n) Transmitters; Emerson.com; Copyright 2021; 2 pages.

TempTrak® Wireless Monitoring 900 MHz Hardware; Emerson.com; 2 pages.

TempTrak™ MX Series Wi-Fi® Data Logger Quick Start Guide; www.copeland.com; 2023; 18 pages.

TempTrak™ MX Series Wi-Fi™ Data Logger; www.cooper-atkins.com; accessed Mar. 28, 2024; 3 pages.

* cited by examiner

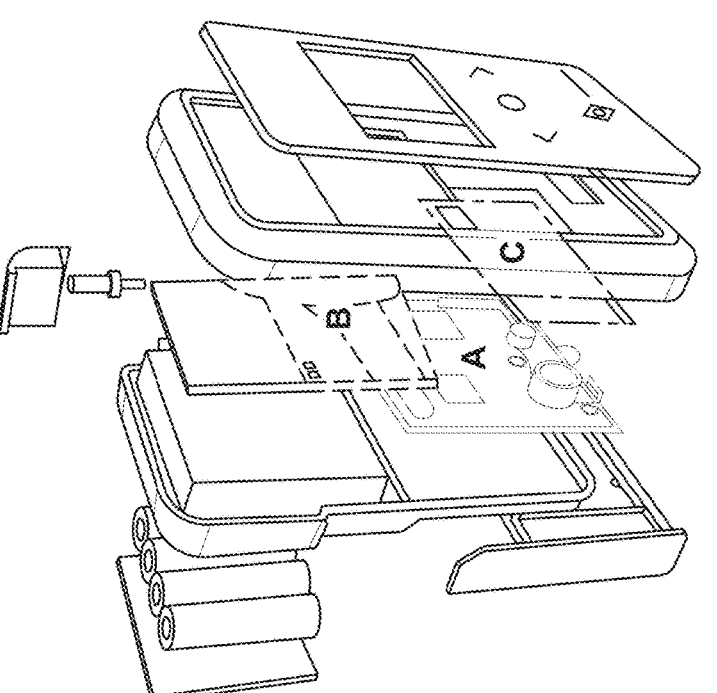

1. The device will have a module design so that the "C" board can be swapped depending on the communication method required by the end user – Wi-Fi, cellular, 900 MHz, *etc.*

2. A single configured device will also be able to wirelessly configure multiple devices via BLUETOOTH communication.

Main Platform board (+BLE)
Can be repackaged in smaller form factor

A

Display Board

B

Expansion board
Can accommodate Wi-Fi/ 900MHz / Cellular

Assembled Unit

BLUETOOTH Configuration Process

Configured Unit

Wi-Fi Data Logger Button Guide

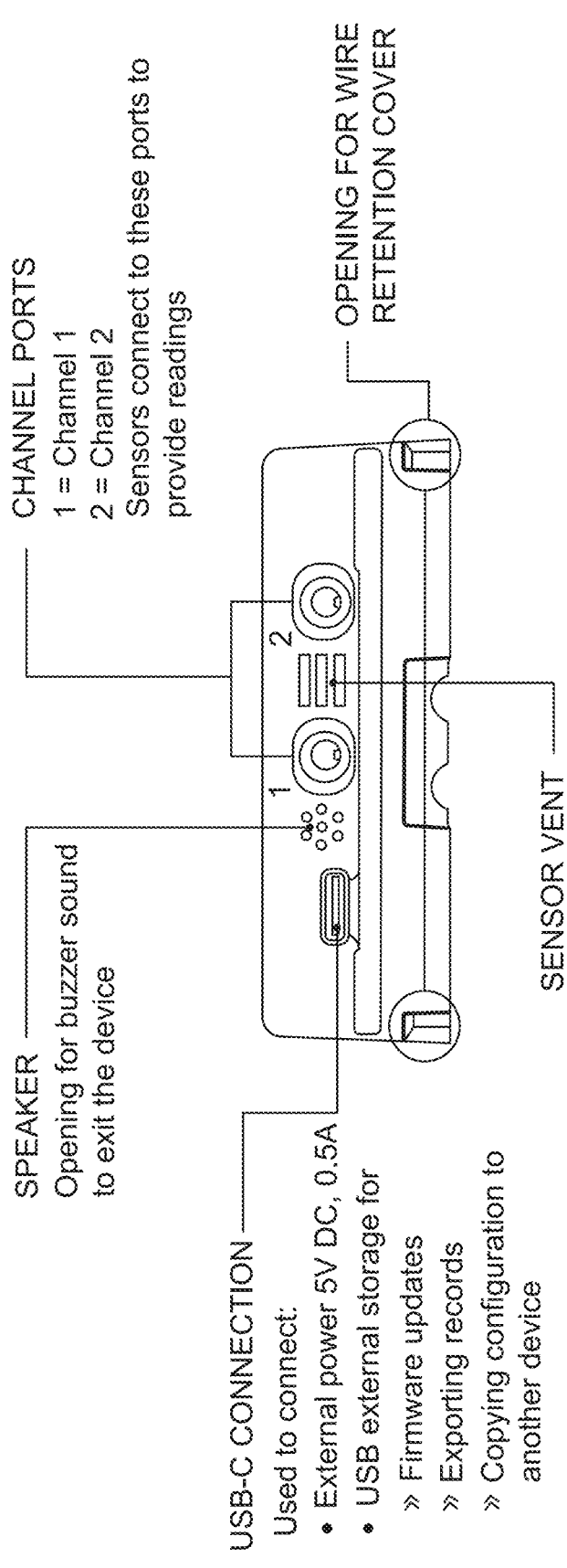

Wi-Fi Data Logger Bottom View

CHANNEL PORTS
1 = Channel 1
2 = Channel 2
Sensors connect to these ports to
provide readings

OPENING FOR WIRE
RETENTION COVER

SPEAKER
Opening for buzzer sound
to exit the device

USB-C CONNECTION
Used to connect:
• External power 5V DC, 0.5A
• USB external storage for
  » Firmware updates
  » Exporting records
  » Copying configuration to
    another device

SENSOR VENT

FIG. 11

Import TempTrak Certificates

NOTE: Please reach out to your I-Care technician to get TempTrak Certificates.

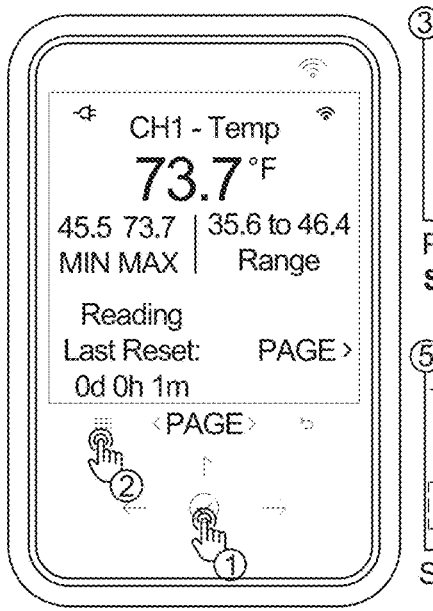

1. Wake device if inactive for 30 seconds or more.

2. Select Settings Menu.

③ Enter Pin

| 0 | 1 | 2 | 3 | 4 |
| 5 | 6 | 7 | 8 | 9 |
| Backspace | | Next | | |

Pin needed to access the Settings Menu.

④ Settings

- General Settings
- Sensor Settings
- Alarm Snooze & Delay

Use down button or page > button to navigate to page 2.

⑤ Settings

- Logging Intervals
- Network Settings
- TempTrak Settings

Select TempTrak Settings.

⑥ TempTrak Settings

- TempTrak Status
- Connect to TempTrak
- Import Certificates

Use navigation buttons to select Import Certificates.

⑦ Import Certificates

Import certificates to securely connect to TempTrak server

Next

⑧ Insert USB

Please insert a USB mass storage Device before continuing.

Next

Cancel

Insert USB external storage device with certificates loaded in the USB port and select Next. SAMSUNG brand USB recommended.

⑨ Import Certificates

Importing cert_ca_pem. Do not remove USB mass storage device.

0%

Progress bar will move to 100% when completed.

⑩ Import Certificates

Certificates have been imported

✓

Finish

FIG. 13

Edit Alarms
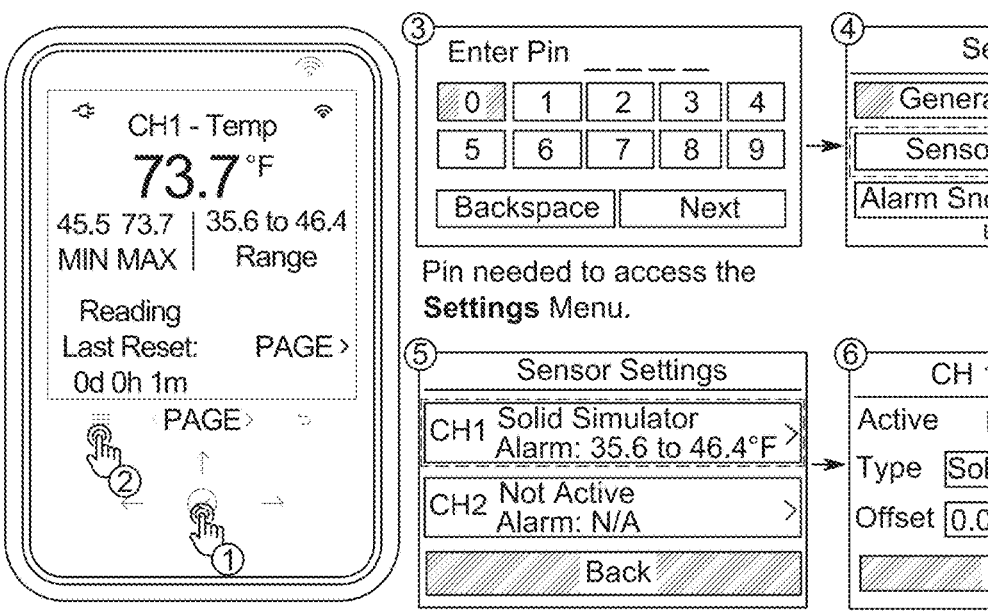
1. Wake device if inactive for 30 seconds or more.
2. Select Settings Menu.
Pin needed to access the Settings Menu.
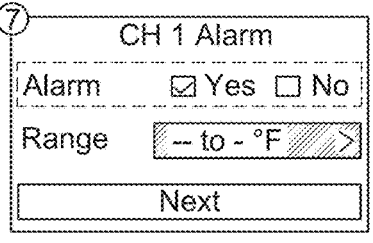
Turn off or on the alarm.
FIG. 14

Customize Transmission Intervals
NOTE: Longer Measure and Transmit Intervals will result in improved battery life.
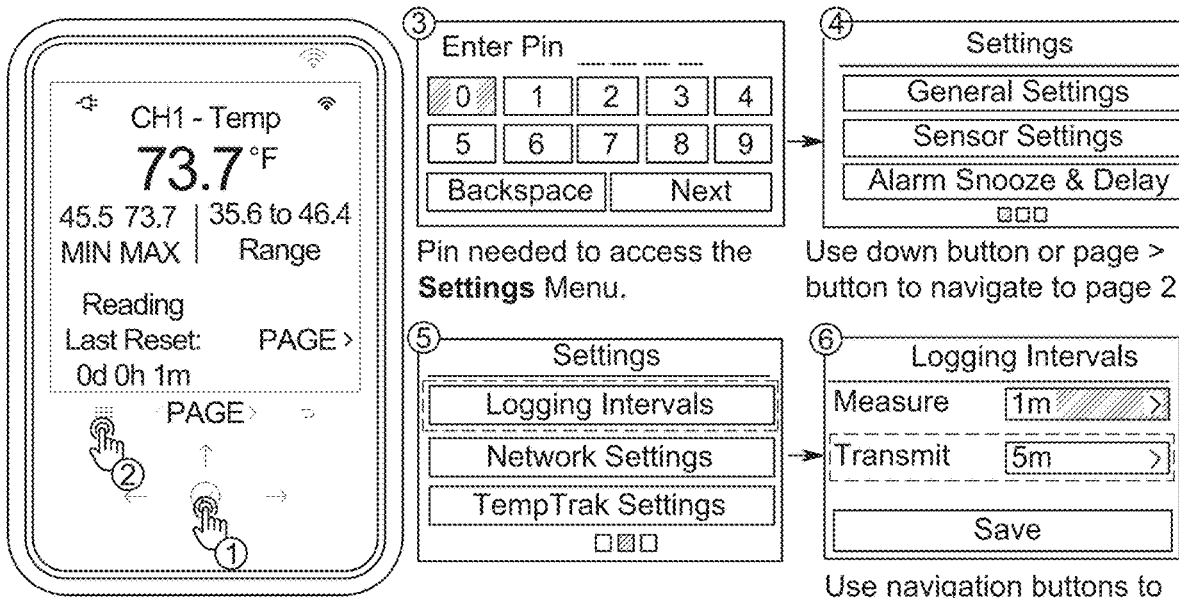
1. Wake device if inactive for 30 seconds or more.
2. Select Settings Menu.
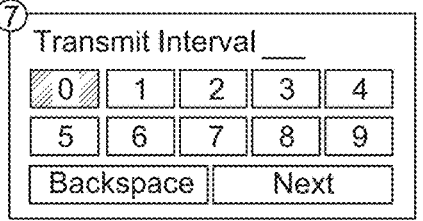
Use navigation buttons to set desired Transmit interval.
FIG. 15

Export Settings to USB

Import Settings from One Device to Another

Registering Devices in TempTrak Software (5.2.5)

Step 1

Choose Sensor Registration from Configuration tab on the left.

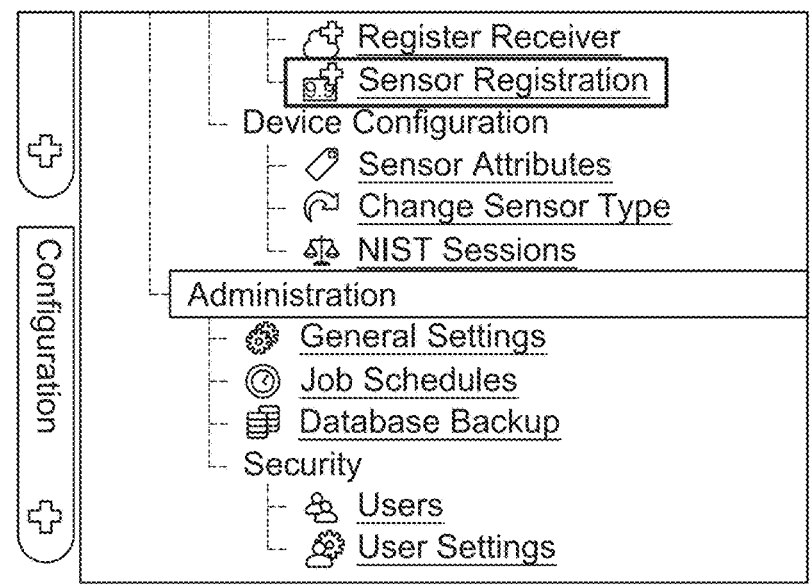

Step 2

Input Sensor ID and Security ID.
These can be found on the label on the back of the device.

| Sensor ID | Security ID | Transmitter Type |
|---|---|---|
| | | Digital Temperature ▼ |

Step 3

Change Transmitter Type from Digital Temperature to either MX40 or MX50 from the transmitter type drop-down menu.

| Sensor ID | Security ID | Transmitter Type |
|---|---|---|
| | | Digital Temperature ▼ |

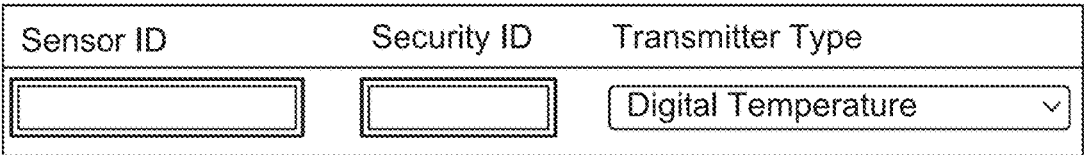

*The model number (MX40-WF or MX50-WF) is listed on the label on the back of the unit.*

FIG. 18

Step 4

Choose the channel and monitoring type from the drop-down menu.

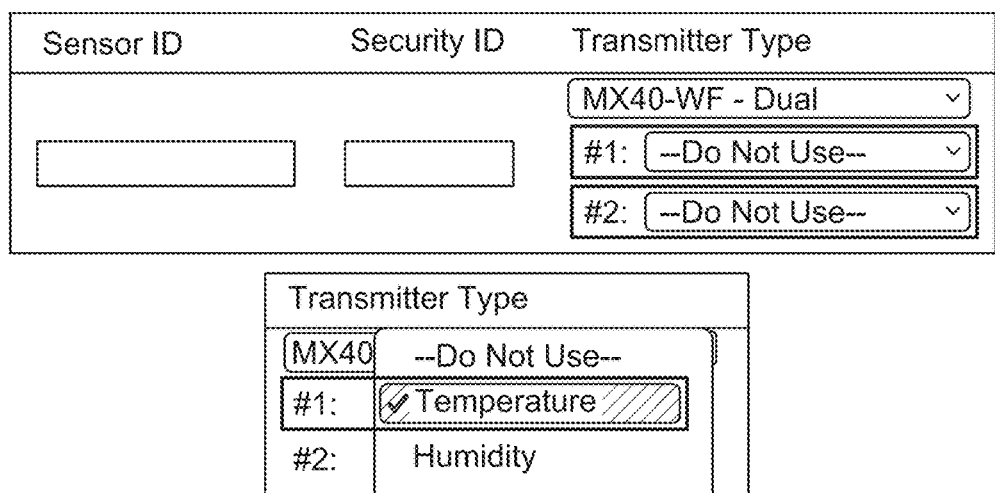

*Select the property to be measured from the drop-down list.*

Step 5

Choose the appropriate group for the sensor to be associated with.

| Sensor ID | Security ID | Transmitter Type | Assign To Group (Optional) |
|---|---|---|---|
| | | MX40-WF - Dual ˅<br>#1: Temperature ˅<br>#2: Temperature ˅ | --Select Group-- ˅ |

*It is recommended to add the sensor to a group. Depending on your view, you may not be able to view or search for a sensor after it is registered depending what view is assigned to your profile.*

Step 6

Repeat steps 1-5 on additional rows to add multiple sensors at once, or you can click the Add button in the bottom right corner to finish and add sensor(s).

FIG. 19

MONITORING ENVIRONMENTAL CONDITIONS OF STORAGE UNITS FOR VACCINES AND OTHER CLIMATE SENSITIVE PRODUCTS

CROSS-REFERENCE TO RELATED APPLICATION

This application claims the benefit of and priority to U.S. Provisional Patent Application No. 63/523,835 filed Jun. 28, 2023. The entire disclosure of the above application is incorporated herein by reference.

FIELD

The present disclosure generally relates to monitoring environmental conditions (e.g., temperature, humidity, carbon dioxide, oxygen, pressure, etc.) of storage units, such as storage units for vaccines, medications, drugs, and other climate sensitive products, etc.

BACKGROUND

This section provides background information related to the present disclosure which is not necessarily prior art.

Lifesaving medications and vaccines must be stored within proper temperature and humidity ranges in order to maintain effectiveness and potency. Accordingly, a wireless environmental monitoring system may be used to take readings at regular intervals and gauge appropriate temperatures based on predetermined thresholds. The wireless environmental monitoring system may generate alerts when temperatures are out of range and create an audit trail, which can help staff better protect patients and improve efficiencies facility-wide.

DRAWINGS

The drawings described herein are for illustrative purposes only of selected embodiments and not all possible implementations, and are not intended to limit the scope of the present disclosure.

FIG. 1 is an exploded perspective view of an exemplary embodiment of an environmental monitoring device operable for monitoring environmental conditions (e.g., temperature, humidity, carbon dioxide, oxygen, pressure, etc.) of storage units for vaccines, medicines, and other climate sensitive products. The environmental monitoring device is configured to have a modular design enabling expansion "C" boards to be swapped or selectively interchanged depending on the communication method (e.g., Wi-Fi, cellular, 900 MHz, etc.) of the end user.

FIG. 11 is a bottom view of the Wi-Fi Data Logger shown in FIG. 8 with the speaker, channel ports, USB-C connection, sensor vent, and opening for wire retention cover according to an exemplary embodiment of the present disclosure.

FIGS. 13 through 19 illustrate an exemplary initial set up process including steps to: Import Certificates (FIG. 13), Edit Alarms (FIG. 14), Customize Transmission Intervals (FIG. 15), Export Settings to USB (FIG. 16), Import Settings from One Device to Another (FIG. 17), and Registering Devices in Software (FIGS. 18 and 19) according to an exemplary embodiment of the present disclosure.

Corresponding reference numerals may indicate corresponding (though not necessarily identical) parts throughout the several views of the drawings.

DETAILED DESCRIPTION

Figure 2:
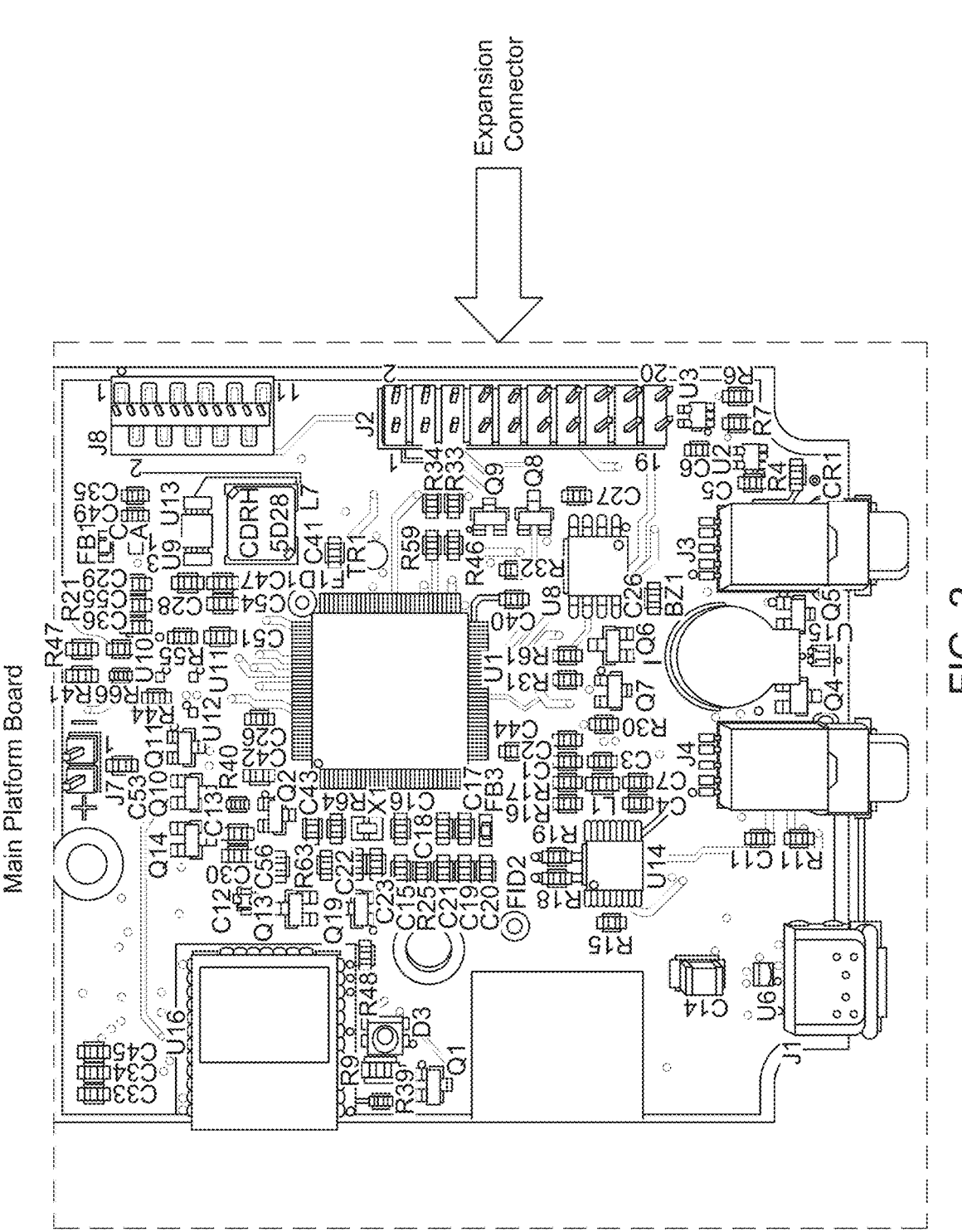
FIG. 2 depicts the main platform "A" board shown in FIG. 1 including its expansion connector of the expansion port header along the main platform board.

Example embodiments will now be described more fully with reference to the accompanying drawings.

Disclosed are exemplary embodiments of environmental monitoring devices for monitoring one or more environmental conditions (e.g., temperature, humidity, carbon dioxide, oxygen, pressure, etc.) of storage units, such as storage units for vaccines, medications, drugs, and other climate sensitive products in a hospital environment or other facility, etc. Also disclosed are exemplary methods of selectively configuring an environmental monitoring device for wireless communication by selectively connecting a communication module, from a plurality of different wireless communication modules, with an expansion port/connector of a printed circuit board of the environmental monitoring device. Further disclosed are exemplary methods of copying a configuration of a first environmental monitoring device to at least one or more other environmental monitoring devices over a wireless communication link.

In an exemplary embodiment, an environmental monitoring device comprises a main printed circuit board (PCB)

having a modular configuration including an expansion port/connector and capable of supporting a display module. A plurality of different communication modules are interchangeably connectible with the expansion port/connector of the main PCB, whereby the environmental monitoring device is selectively configurable for wireless communication according to different wireless protocols depending on which of the different wireless communication modules is selectively connected with the expansion port/connector of the main PCB.

In an exemplary embodiment, an environmental monitoring device comprises a main printed circuit board (PCB) including a wireless communication interface. The wireless communication interface is operable for establishing a wireless communication link with a mobile device for enabling the mobile device to be useable over the wireless communication link for programming and/or configuring the environmental monitoring device. Additionally or alternatively, the environmental monitoring device is a first environmental monitoring device that includes the wireless communication interface for establishing a wireless communication link with at least a second environmental monitoring device whereby the first environmental monitoring device is operable for initiating copying of the configuration of the first environmental monitoring device to the second environmental monitoring device via the wireless communication link.

In exemplary embodiments, the environmental monitoring device is configured to provide alerts (e.g., generate audible alarm, etc.) to out-of-range conditions and reporting the data for documentation. In exemplary embodiments, the environmental monitoring device is configured or specifically designed to meet the Data Logger requirements found in the Vaccine for Children program outlined by the Central for Disease Control (CDC).

Exemplary embodiments are built or configured as a platform and aspects of the environmental monitoring device may be for environmental monitoring in other industries such as food service, data logger for Cargo cryogenic applications, food safety applications, etc.

In exemplary embodiments, an environmental monitoring Internet of Things (IoT) platform includes a device having a modular design. The device is configured such that modular expansion boards ("C" board (FIG. 1), 900 MHz communication module (FIG. 3), Wi-Fi communication module (FIG. 4), etc.) can be swapped out or interchanged depending on the communication method (e.g., Wi-Fi, cellular, 900 MHz, etc.) of the end user. The device includes a modular base or main platform board (e.g., main platform "A" board in FIGS. 1 and 2, etc.) having an expansion port header including an expansion connector. The device is capable of supporting different communications technologies through the expansion port header of the main platform board and an LCD interface through the display board (e.g., "B" board (FIG. 1), display module (FIG. 5), etc.). Different modular expansion boards (e.g., 900 MHz communication module (FIG. 3), Wi-Fi communication module (FIG. 4), etc.) can be selectively interchangeably connected with the expansion connector of the expansion port header along the main platform board. With its modularity, the device is able to support future wireless technologies over the same interface by selectively interchangeably connecting a new module board design configured for the future wireless technology to the expansion connector of the expansion port along the main platform board. In exemplary embodiments, the device includes a separate panel for a display, such that some device models will have a display while other device models will not have a display.

In exemplary embodiments, the main platform board may be configured (e.g., include a BLUETOOTH radio, etc.) to enable the device to communicate with other device(s) via BLUETOOTH short-range wireless communication protocol or other short-range wireless communication protocol. In such exemplary embodiments, the single configured device may be operable with the capability to wirelessly configure multiple devices via BLUETOOTH short-range wireless communication protocol (e.g., BLUETOOTH Low Energy (BLE), etc.).

In exemplary embodiments (e.g., FIG. 7, etc.), environmental monitoring devices are configured to be operable with local device to local device configuration over BLUETOOTH short-range wireless communication protocol or other short-range wireless communication protocol. In such exemplary embodiments, a single configured device may be able to wirelessly configure multiple devices via Bluetooth communication without having to go through the configuration menu again. The programmed environmental monitoring device initiates copying its configuration to another monitoring device via Bluetooth connection. The configuration process is triggered through on screen navigation. And the environmental monitoring device wirelessly configures multiple devices through the BLUETOOTH radio on the main circuit board of the environmental monitoring device. Other radios (e.g., Wi-Fi, 900 MHz, etc.) are on "plug in" daughter boards (e.g., 900 MHz communication module (FIG. 3), Wi-Fi communication module (FIG. 4), etc.) that are selectively interchangeably connectable (e.g., individually, only one at a time, etc.) with the main circuit board of the environmental monitoring device.

FIG. 1 is an exploded perspective view of an exemplary embodiment of an environmental monitoring device operable for monitoring environmental conditions (e.g., temperature, humidity, carbon dioxide, oxygen, pressure, etc.) of storage units for vaccines, medicines, and other climate sensitive products. The environmental monitoring device is configured to have a modular design enabling expansion "C" boards to be swapped or selectively interchanged depending on the communication method (e.g., Wi-Fi, cellular, 900 MHz, etc.) of the end user. The device includes a main platform "A" board and a display "B" board. The main platform "A" board includes an expansion port header with expansion connectors to which are selectively connectable expansion connectors of the expansion "C" boards (e.g., expansion boards that can accommodate Wi-Fi, cellular, 900 MHz, etc.). The main platform "A" board includes a BLUETOOTH Low Energy (BLE) radio that enables the single configured device to be able to wirelessly configure multiple devices via BLUETOOTH communication. The main platform "A" board can be repackaged in a smaller form factor.

FIG. 2 depicts the main platform "A" board shown in FIG. 1 including its expansion connector of the expansion port header along the main platform board.

Figure 3:
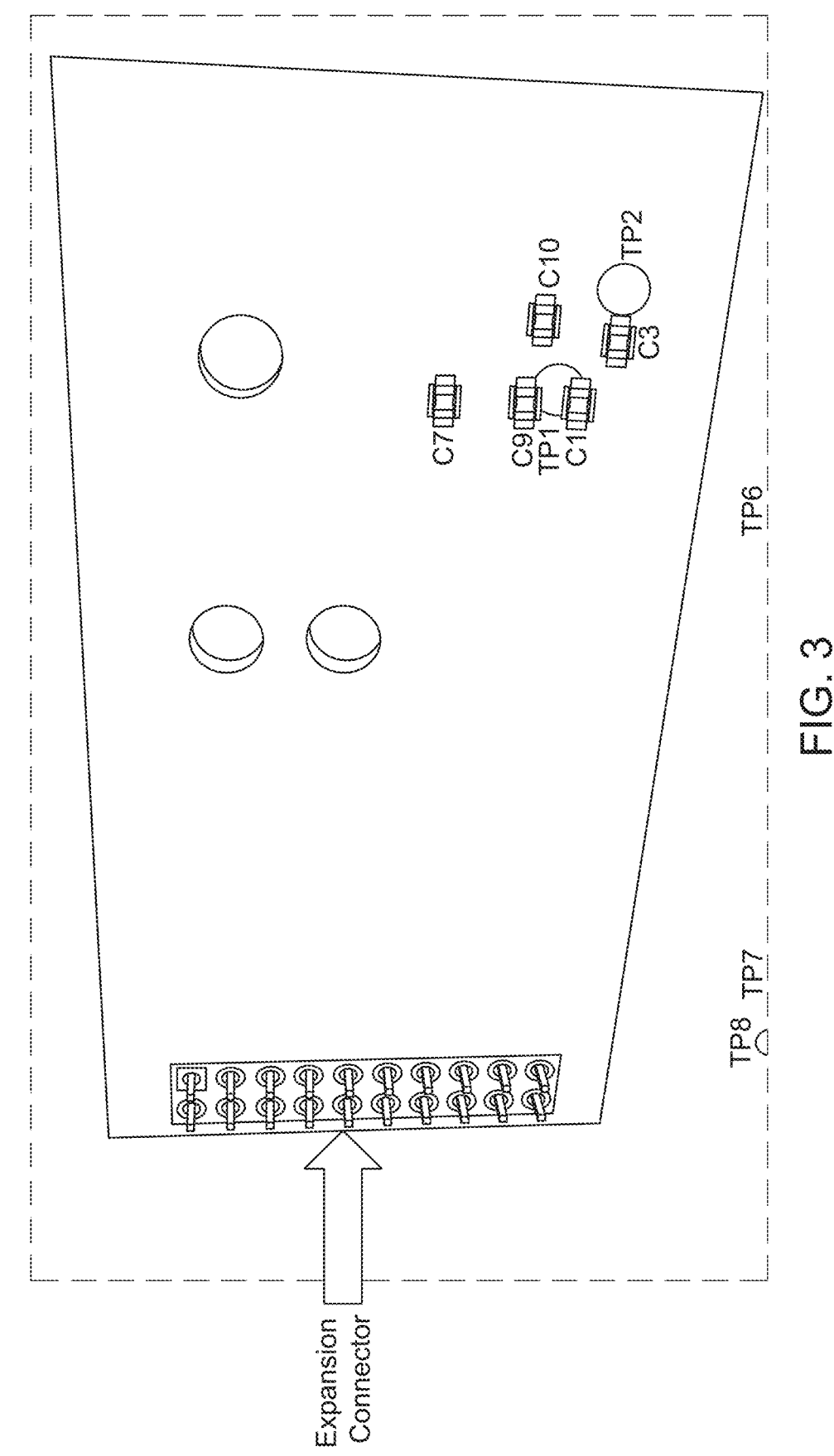
FIG. 3 depicts a 900 MHz communication module (900 MHz expansion "C" board shown in FIG. 1) including its expansion connector that is selectively connectable with the expansion connector of the main platform board shown in FIG. 2 to thereby configure the device shown in FIG. 1 for 900 MHz communications.

FIG. 3 depicts a 900 MHz communication module (900 MHz expansion "C" board shown in FIG. 1) including its expansion connector that is selectively connectable with the expansion connector of the main platform board shown in FIG. 2 to thereby configure the device shown in FIG. 1 for 900 MHz communications.

Figure 4:
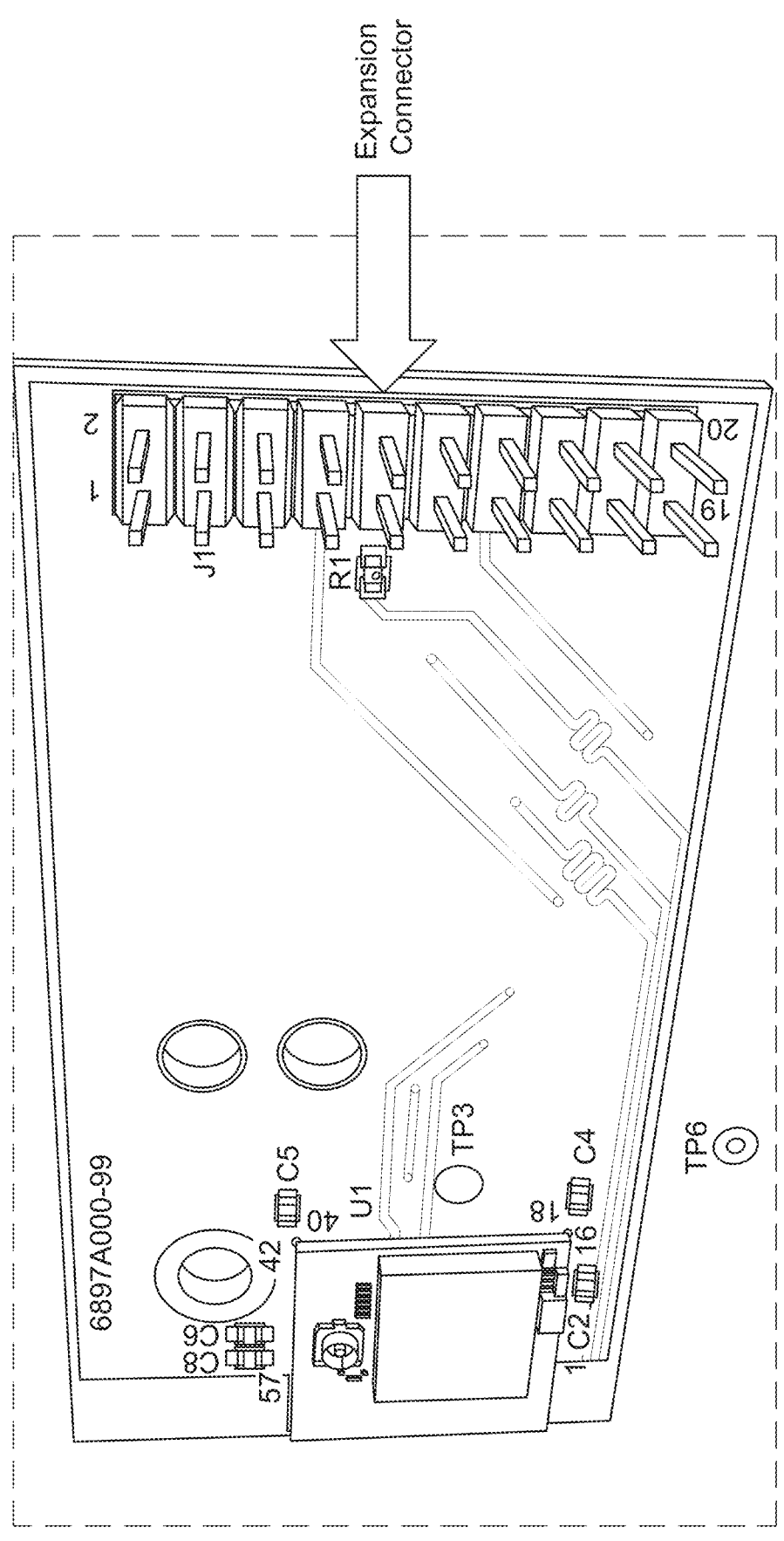
FIG. 4 depicts a Wi-Fi communication module (Wi-Fi expansion "C" board shown in FIG. 1) including its expansion connector that is selectively connectable with the expansion connector of the main platform board shown in FIG. 2 to thereby configure the device shown in FIG. 1 for Wi-Fi communications.

FIG. 4 depicts a Wi-Fi communication module (Wi-Fi expansion "C" board shown in FIG. 1) including its expansion connector that is selectively connectable with the expansion connector of the main platform board shown in FIG. 2 to thereby configure the device shown in FIG. 1 for Wi-Fi communications.

Figure 5:
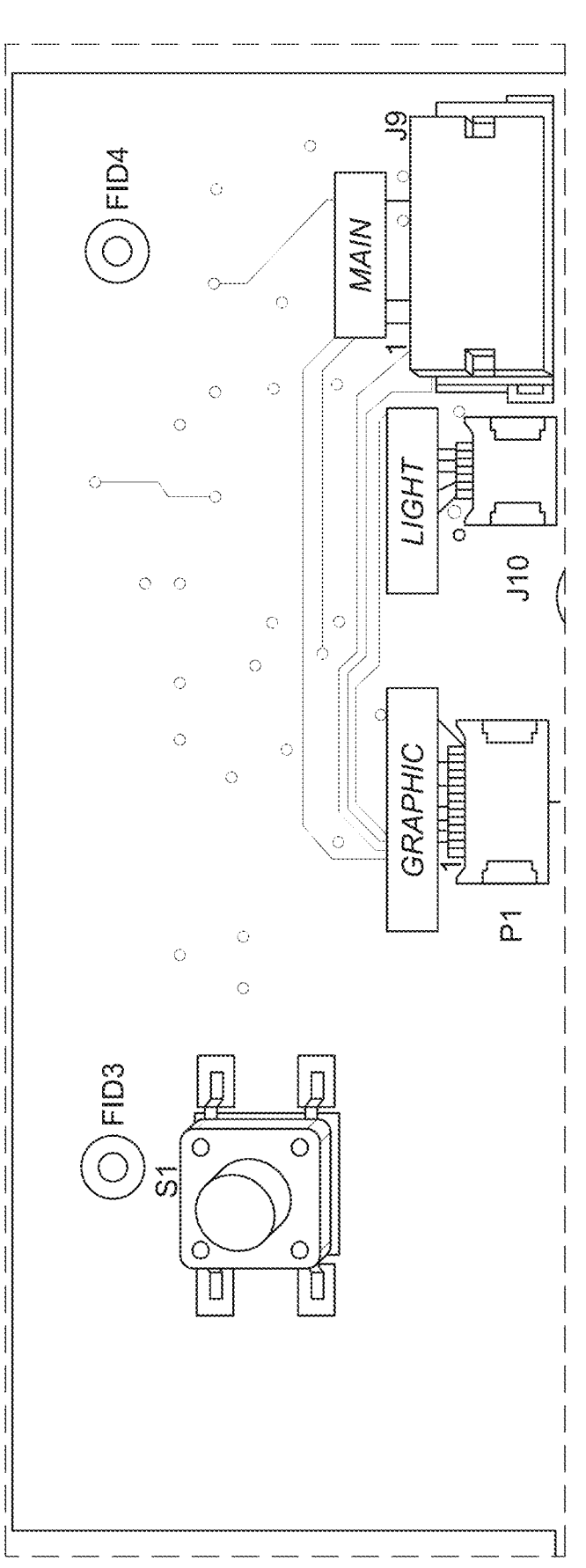
FIG. 5 depicts a display module (display "B" board shown in FIG. 1) that may be used for providing an LCD interface for the device shown in FIG. 1.

FIG. 5 depicts a display module (display "B" board shown in FIG. 1) that may be used for providing an LCD interface for the device shown in FIG. 1.

Figure 6:
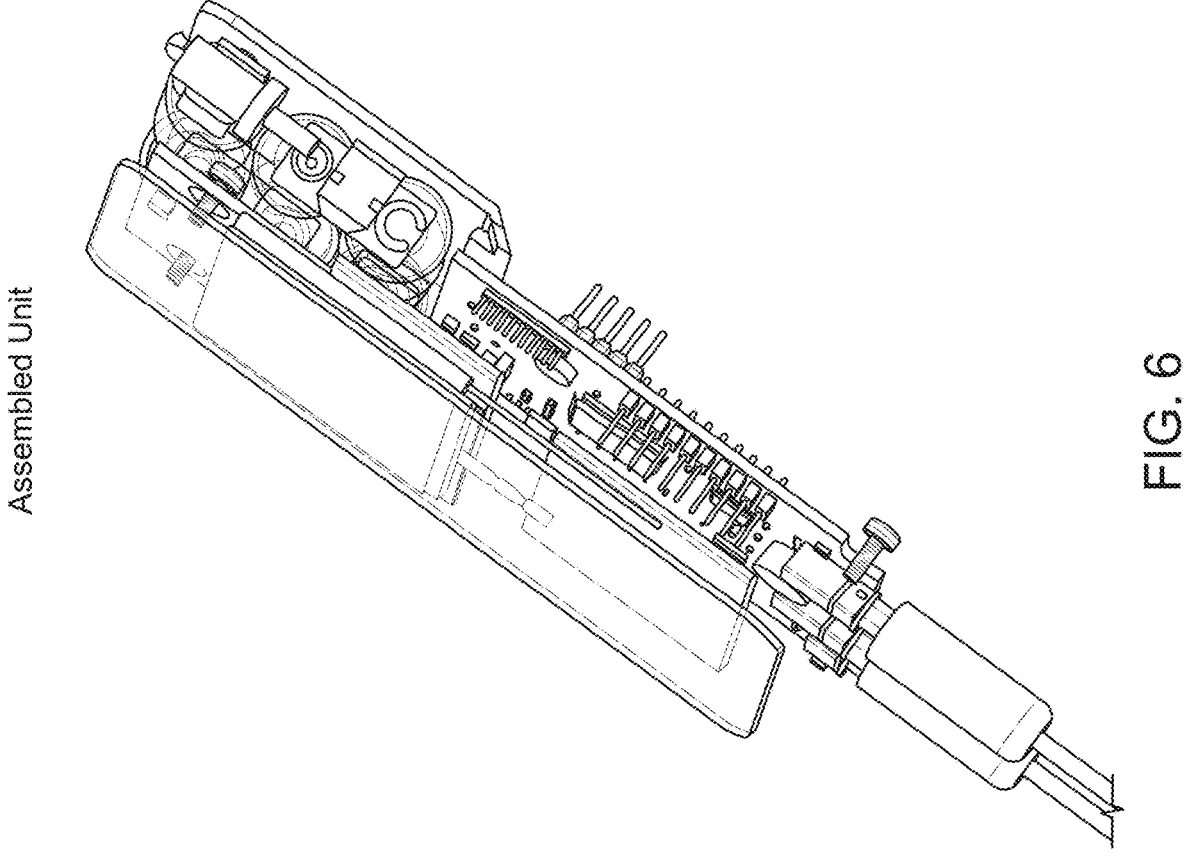
FIG. 6 depicts an assembled device for monitoring environmental conditions, which device has a modular design enabling expansion "C" boards to be swapped or selectively interchanged depending on the communication method (e.g., Wi-Fi, cellular, 900 MHz, etc.).

FIG. 6 depicts an assembled device for monitoring environmental conditions, which device has a modular design enabling expansion "C" boards to be swapped or selectively interchanged depending on the communication method (e.g., Wi-Fi, cellular, 900 MHz, etc.).

Figure 7:
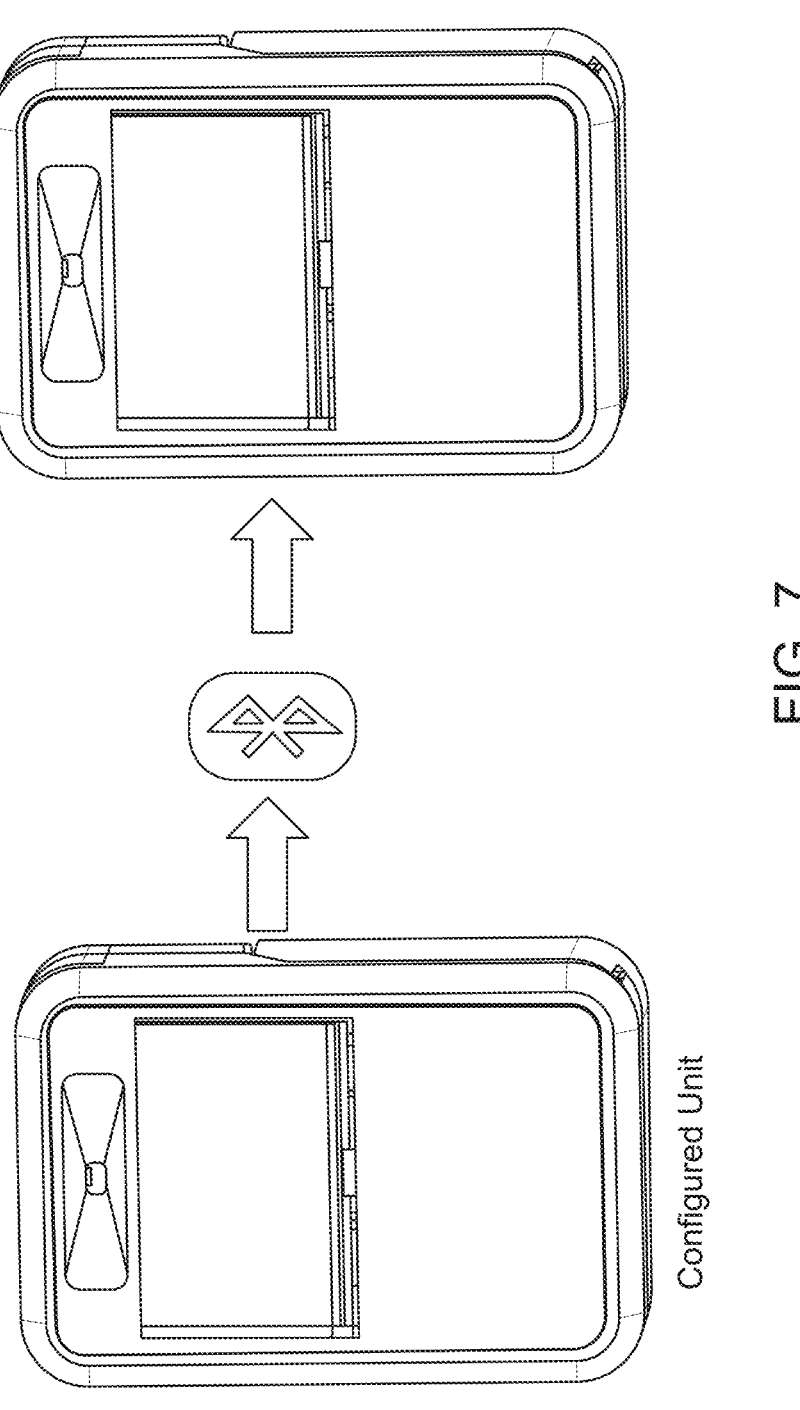
FIG. 7 depicts a BLUETOOTH configuration process according to an exemplary embodiment in which a single configured device is configured with the ability to wirelessly configure multiple devices via BLUETOOTH communication.
Figure 8:
FIG. 8 shows an exemplary embodiment of an environmental monitoring device comprising a Wi-Fi Data Logger.
Figure 9:
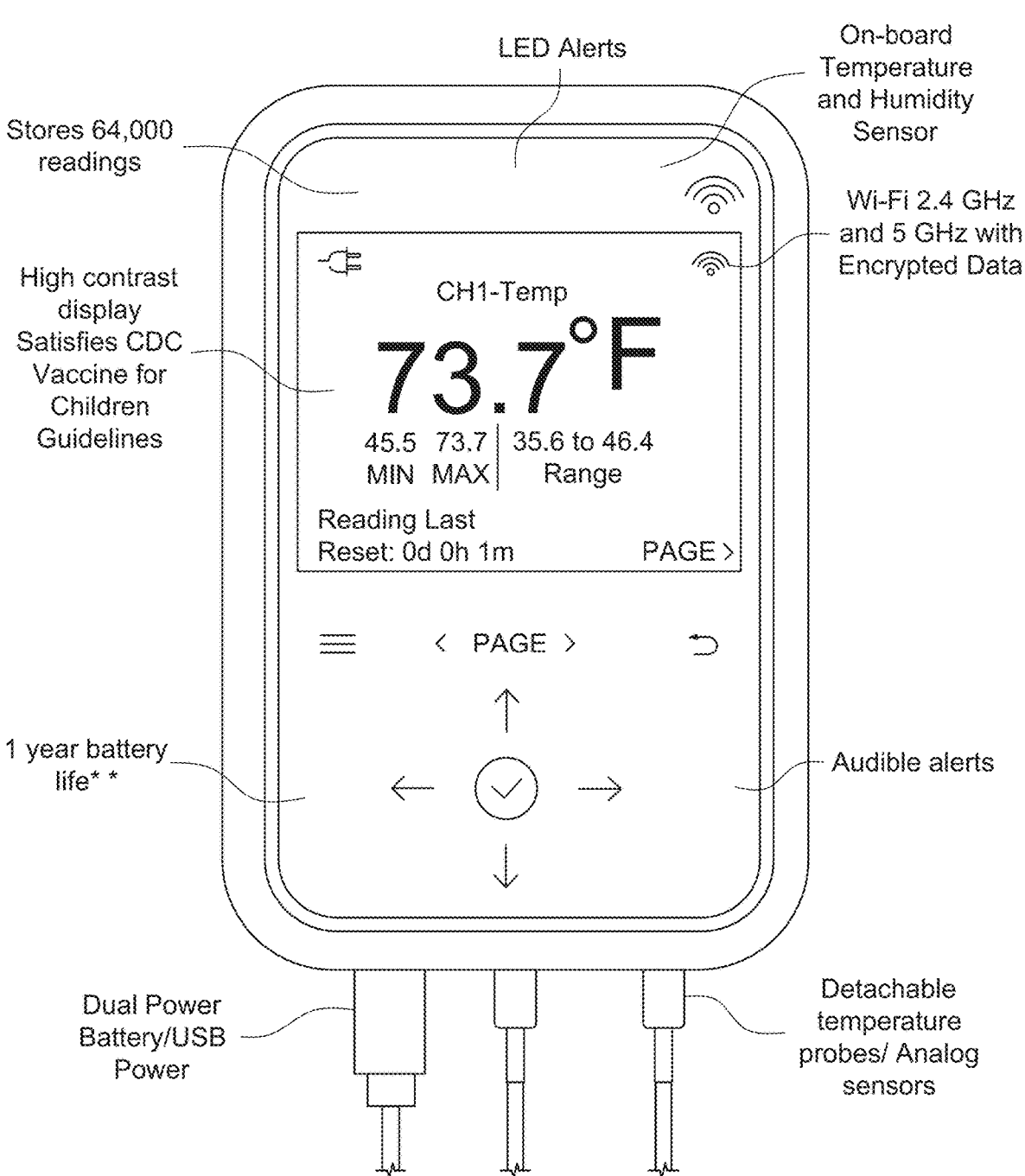
FIG. 9 shows the Wi-Fi Data Logger shown in FIG. 8 with various exemplary features identified according to an exemplary embodiment of the present disclosure.
Figure 10:
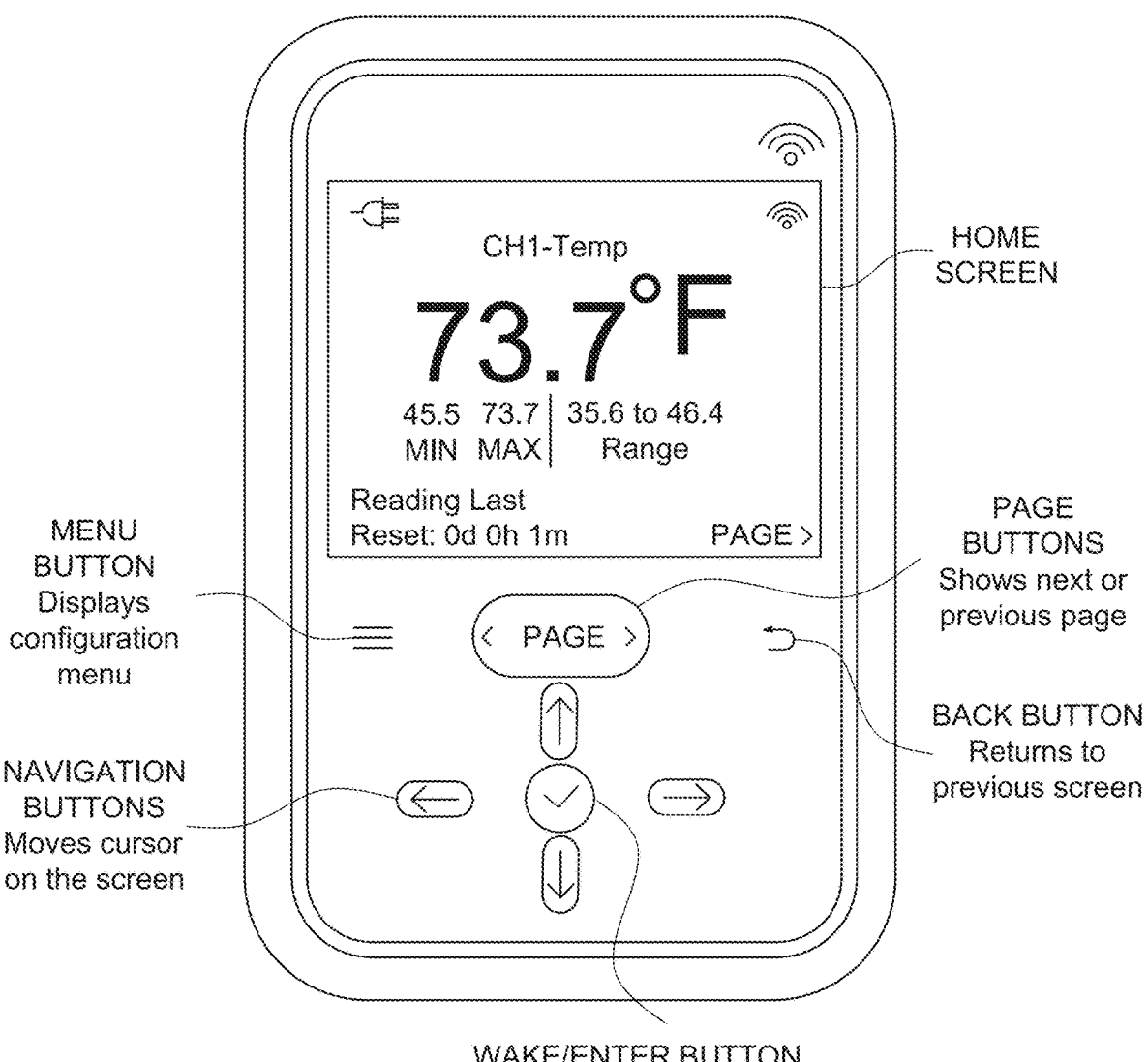
FIG. 10 shows the Wi-Fi Data Logger shown in FIG. 8 with the user interface features identified, specifically, home screen, menu button, navigation buttons, wake/enter button, back button, and page buttons according to an exemplary embodiment of the present disclosure.
Figure 12:
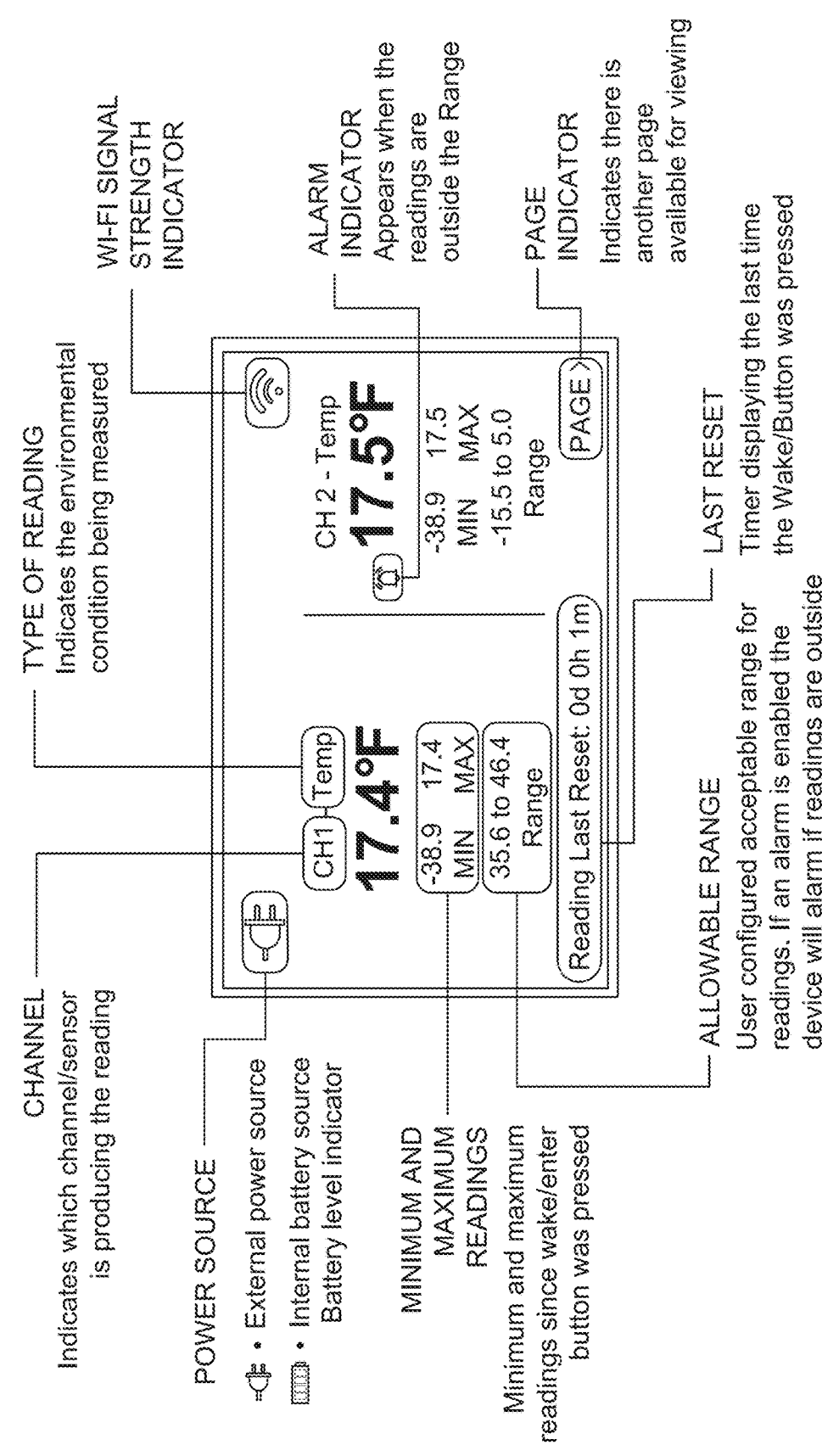
FIG. 12 shows an Icon Guide for the Wi-Fi Data Logger shown in FIG. 8 including channel, type of reading, Wi-Fi signal strength, alarm indicator, page indicator, last reset, allowable range, minimum and maximum readings, and power source according to an exemplary embodiment of the present disclosure.

FIG. 7 depicts a BLUETOOTH configuration process according to an exemplary embodiment in which a single configured device is configured with the ability to wirelessly configure multiple devices via BLUETOOTH communication.

Appendix A of U.S. Provisional Patent Application No. 63/523,835 filed Jun. 28, 2023 includes screenshots of an environmental monitoring device showing interactive screens that may be displayed during a device configuration process according to exemplary embodiments of the present disclosure. The contents of Appendix A is incorporated herein by reference in its entirety.

When the demo is opened on a mobile device, the user may be prompted to either connect a gamepad or keyboard. Additionally, or alternatively, implementing the input simulation of a keypad may include a mock keypad or touch-based user interface. The mock keypad may enable the user to navigate around the mock keypad. But the mock keypad would not enable input of any characters and the user interface would proceed to the next interactive screen when the user clicks next or proceed. For the touch-based user interface, the buttons one the device screen would be clickable or tappable. The user would be able to navigate the user interface using the left, up, down, right arrow ← ↑ ↓ → keys. The user can select an interaction by pressing the ↵ (Enter) key. And the user can go back one screen by pressing backspace.

In Appendix A, the following parameters were used for purposes of example only including:

Default pin: 0123
New pin: 0000
Time: 5:45
Network Name: EM3RSON2022!
Network Password: 123456789
IP address: 192.168.2.1

By way of example, an exemplary embodiment of an environmental monitoring device disclosed herein may include one or more of the features disclosed in Appendix B of U.S. Provisional Patent Application No. 63/523,835 filed Jun. 28, 2023 for the TEMPTRACK Wi-Fi (802.11 b/g/n) Transmitters. The contents of Appendix B is incorporated herein by reference in its entirety. For example, an exemplary embodiment of an environmental monitoring device may comprise a Wi-Fi (802.11 b/g/n) transmitter that is a high speed wireless module with PEAPv0 enterprise security, capable of collecting, storing and transmitting data wirelessly over a standard 802.11 b/g/n (Wi-Fi—RF Frequency 2.4 to 2.497 GHz) with UDP protocol. The transmitter is operable for passing information to an application located on a Wi-Fi-enabled network. Each transmitter is operable for monitoring against preset conditions defined by the user and can provide audio and visual alerts. Additional alerts can be provided through a variety of methods such as pager, cellphone, and e-mail, etc. Information recorded (in ° F. and ° C.) to a database is timestamped and cannot be altered through the user interface. All transmitters can be configured for Wi-Fi and server networks as well as sample transmit intervals. The transmitter will connect to a Wi-Fi IP network and send data to the designated server. Both Wi-Fi (802.11 b/g/n) and 900 MHz transmitters can communicate within a single installation. And on-site NIST traceability may be available.

The Wi-Fi transmitters may support the following security modes: WEP, WPA-PSK, WPA2-PSK, WPA2-Enterprise with PEAPv0 and EAP-MSCHAPv2. PEAPv0 wireless security may be implemented for protecting customers' data transferred between clients and servers, preventing unwanted access to secured networks even if the threat is posing as a transmitter. PEAPv0 with EAP-MSCHAPv2 is the most common form of PEAP in use and one of the most widely supported EAP standards in the world. PEAP reduces the number of SSIDs required because the transmitters can reside on a PEAP network normally reserved for internal data transfer.

Continuing with this example, the exemplary embodiment of the environmental monitoring device may be configured to include one or more of (but not necessarily any or all) of the following exemplary features: connects to existing Wi-Fi IP network, speed: Wi-Fi 802.11 b/g/n 72 Mbit/sec, enterprise security: PEAPv0 with EAP-MSCHAPv2 (PEAP), radio protocol: IEEE 802.11 b/g/n compatible, RF frequency: 2.4 to 2.497 GHz, operating environment: 0° to 140° F. (−17° to 60° C.), up to 95% relative humidity (RH), battery: two 3.6V AA lithium batteries, battery life: 14-15 months (based upon a 15 minute transmit and sample cycle and good signal), external power supply (Micro-USB) with battery backup, on-transmitter buffer storage size of 4,096 samples, visual and audio alarm indicators—can be manually cleared with reset feature, ABS plastic enclosure, wall-mounting: tape or screw-mount, and/or certifications: FCC, CE, IC, and RoHS compliant.

With further reference to this example, the exemplary embodiment of the environmental monitoring device may be configured to provide one or more of (but not necessarily any or all) of the following exemplary benefits: utilizes infrastructure already in facility, optimized for network speed, higher security network protects real-time data traffic, industry standard RF frequency, can be placed in a variety of environments, common battery size, less frequent battery replacements, reconfigure Wi-Fi transmitters over the air, reduces maintenance, ensures continuous data collection in the event of network outage, ensures no alerts go unanswered, durable casing protects inner circuitry, and/or ensures secure mounting for different equipment.

By way of further example, an exemplary embodiment of an environmental monitoring device disclosed herein may include one or more of the features disclosed in Appendix C of U.S. Provisional Patent Application No. 63/523,835 filed Jun. 28, 2023 for the TEMPTRACK Wireless Monitoring 900 MHz hardware. The contents of Appendix C is incorporated herein by reference in its entirety. For example, an exemplary embodiment of an environmental monitoring device may comprise a 900 MHz transmitter configured to operate on a 900 MHz frequency-hopping spread spectrum with an open-field range of up to 2,500 ft and a typical interior range of up to 500 ft. Each transmitter is battery operated and monitors against preset conditions that are user-defined within an application. Information recorded to a database (° F./C) is time stamped and cannot be altered through the user interface. Transmitters calibrated to NIST standards are available.

Continuing with this example, the exemplary embodiment of the environmental monitoring device may be configured to include one or more of (but not necessarily any or all) of the following exemplary features: bandwidth Range: 902-928 MHz (US), 868-870 MHz, (Europe), storage on intellibase buffer during power outages if buffer and receiver are on UPS, ABS plastic enclosure, wall-mounting: double sided, high strength tape or screw-mount, power: 2/3A Lithium battery, 3V, and/or battery life: 2.5-3 years.

With further reference to this example, the exemplary embodiment of the environmental monitoring device may be configured to provide one or more of (but not necessarily any or all) of the following exemplary benefits: longer range than Wi-Fi, does not compete with other networks for bandwidth, data is buffered and recoverable if network or power fails, durable casing protects inner circuitry, and/or can be easily transferred to a new location.

By way of example, an environmental monitoring device disclosed herein may include one or more of the features disclosed in Appendix 1 filed herewith that is titled TEMPTRACK MX Series Wi-Fi Data Logger. The contents of Appendix 1 is incorporated herein by reference in its entirety. As disclosed in Appendix 1, an exemplary embodiment may comprise one or more Wi-Fi data loggers that are part of an environmental monitoring system. The Wi-Fi data loggers are high speed wireless modules with WPA2-Enterprise security, capable of collecting, storing and transmitting data wirelessly. The data logger sends information on common Wi-Fi frequencies (2.4 GHz and 5 GHz) to an application located on a Wi-Fi-enabled network. Each data logger monitors against preset conditions that are defined by the user and can provide audio and visual alerts to enable quick corrective actions. Additional alerts can be provided through a variety of methods such as cellphone, and e-mail, etc. Information recorded (in ° F. and ° C.) to a database is timestamped reducing the potential for human error. In addition to the onboard temperature and humidity sensors, the Wi-Fi data logger is designed to accommodate 1-2 detachable temperature probes and analog sensors depending on the model.

With its built-in visual display, the versatile, multi-function data logger my include or provide one or more (but not necessarily any or all) of the following features:

Dual Band Wi-Fi: Experience seamless connectivity in any environment with compatibility across both 2.4 GHz and 5 GHz bands.

Optional Antenna: Ensure reliable connectivity even in areas with weak signals, thanks to the flexibility of an optional antenna.

Secure Configuration Cloning: Expedite system setup with secure cloning of configuration settings, enabling faster deployment and operational efficiency.

On-Screen Configuration: Streamline the setup process with an intuitive on-screen interface, making configuration effortless and user-friendly.

With further reference to this example, the exemplary embodiment of the environmental monitoring device may be configured to provide one or more of (but not necessarily any or all) of the following exemplary benefits:

Reduced costs and reduced complexity with a multi-function device featuring detachable temperature probes and analog sensors able to monitor internal and external temperature, internal humidity and more with analog and contact sensors.

Audible and LED alerts from the data logger along with real-time notifications via mobile device or PC enable staff to take immediate action when conditions fall outside of safe parameters, helping mitigate high-cost temperature events.

Integrated, high-contrast display helps ensure compliance with Vaccines for Children (VFC) guidelines.

Common battery size and increased battery capacity for simple and less frequent battery replacements.

Continuous data collection with automatic backfilling of data in the event of network outage. Storing 64,000 readings for peace of mind and regulatory compliance.

Higher security protocols protect real-time data traffic.

With continued reference to this example, the exemplary embodiment of the environmental monitoring device may be configured with one or more of (but not necessarily any or all) of the following specifications:

Environment

Operating Temperature Range: −4° C. to 140° C.

Humidity: 5% RH to 95% RH, non-condensing

Data logger Memory: Stores 64,000 records, 3 MB

Physical and Mechanical

Dimensions (L×W×H): 5 in×3.4 in×0.9 in

Weight: 242 g

Connectors: 1×USC-C, 2×Phono (audio jack)

Electrical

Battery: Three AA 1.5 V Lithium Batteries, user replaceable

Battery Life: 1 year at 30-minute transmission intervals (battery life will depend on communication interval, network conditions and environmental conditions including operating temperature)

External Power (USB-C Interface): 5V/500 mA

Audio & Visual Indications

Audio: Buzzer: 85 dBA minimum output

LEDs: Single dual color LED

Display: 2.7 inch Memory LCD

Wi-Fi and General Specifications

Communication: Wi-Fi 802.11 b/g/n, 2.4 GHz and 5 GHz

Range: Up to 80 meters indoors (communication range will depend on RF environment)

Wi-Fi Security Mode: WPA2-PSK, WPA2-Enterprise (EAP-TLS, EAPTTLS, EAP-PEAP)

Logging or Transmission Rates: 1-30 minutes

Certifications: FCC, RoHS, WEEE

Temperature Accuracy 0° C.-65° C.±0.4° C.; ±1.0° C., under 0° C. and over 65° C.

Humidity Accuracy at 25° C. 10% RH-90% RH±3.5%; ±5% under 10% RH and over 90% RH.

By way of example, an environmental monitoring device disclosed herein may include one or more of features and/or product specifications disclosed in Appendix 2 filed herewith that is titled TEMPTRACK MX Series Wi-Fi Data Logger Quick Start Guide. The contents of Appendix 2 is incorporated herein by reference in its entirety.

FIGS. 13 through 19 illustrate an exemplary initial set up process including steps to: Import Certificates (FIG. 13), Edit Alarms (FIG. 14), Customize Transmission Intervals (FIG. 15), Export Settings to USB (FIG. 16), Import Settings from One Device to Another (FIG. 17), and Registering Devices in Software (FIGS. 18 and 19) according to an exemplary embodiment of the present disclosure.

During the initial setup, the user follows menu prompts to set-up device. The Factory PIN may be 0 0 0 0. During start-up, the user will need to create a new PIN, which is unrecoverable and should be kept safe. Losing the PIN will require a factory reset to access the menus. To trigger a factory reset, press and hold the center button during power-up. To set the time accurately, the device is synchronized with an NTP server. When importing settings from one device to another, all settings transfer including the NTP settings but manually set times do not. To save time, import the settings of one device to another device using the import settings feature and a USB storage device.

Figure 16:
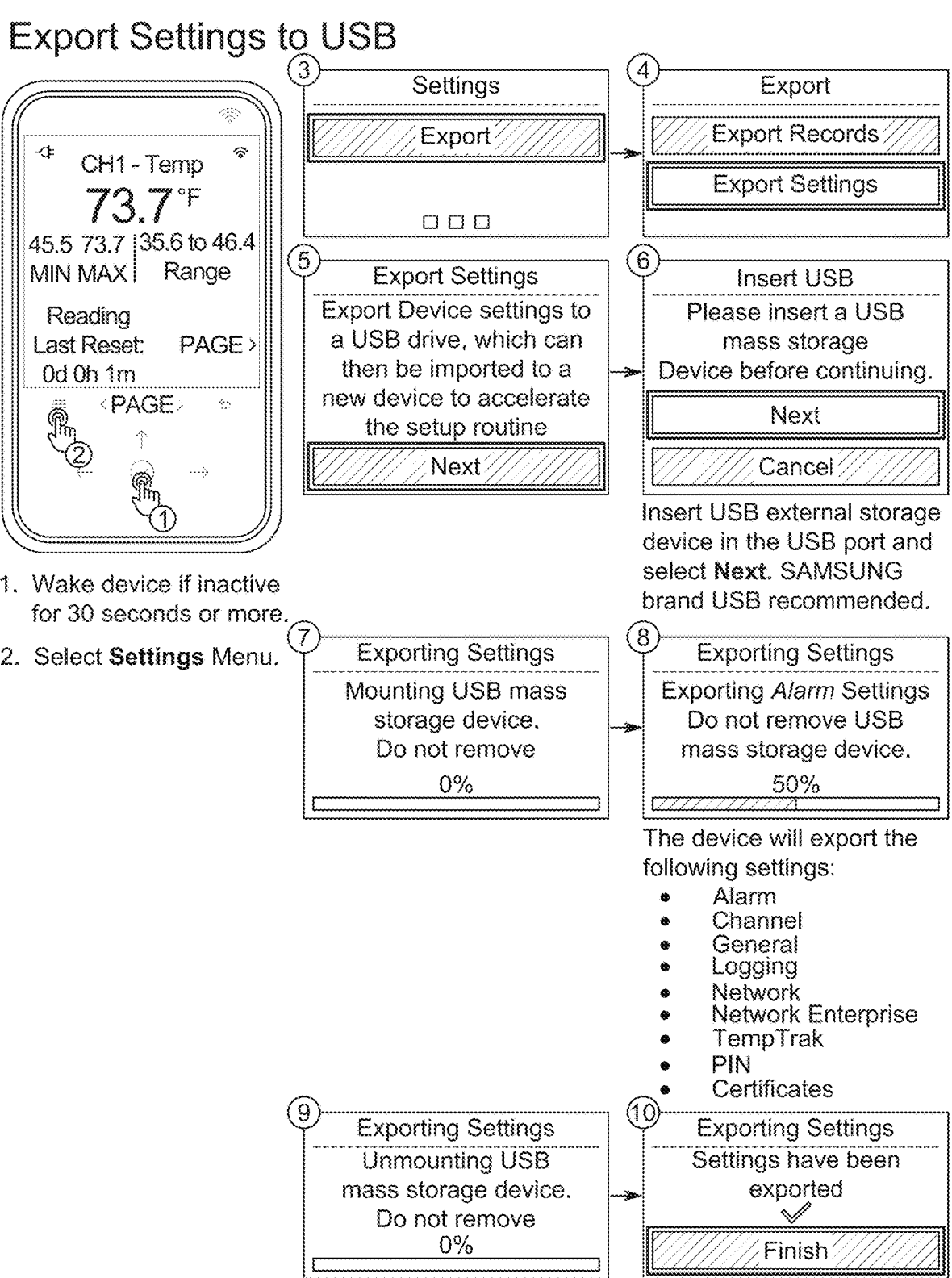
Figure 17:
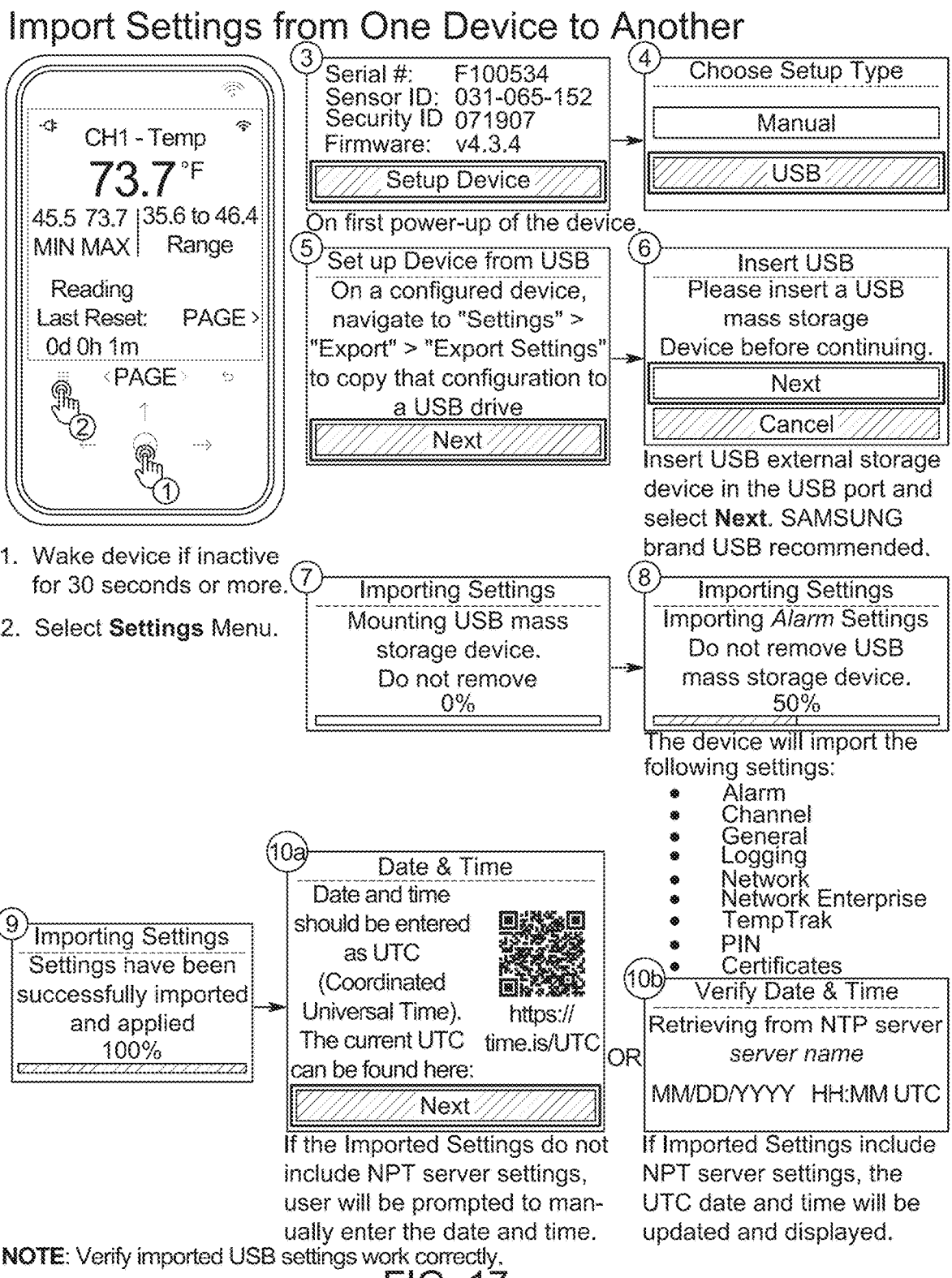

FIG. 13 illustrates an exemplary process for importing certificates that includes the following steps:

1. Wave device if inactive for 30 seconds or more
2. Selecting Settings Menu
3. Enter PIN to access the Settings Menu
4. Navigate to page 2 using the down button or page>button
5. Select TEMPTRACK Settings
6. Use navigation buttons to select Import Certificates
7. Import Certificates
8. Insert USB external storage device with certificates loaded in the USB port and select Next
9. Progress bar will move to 100% when completed
10. Finish—Certificates have been imported FIG. 14 illustrates an exemplary process for editing alarms that includes the following steps:

1. Wave device if inactive for 30 seconds or more
2. Selecting Settings Menu
3. Enter PIN to access the Settings Menu
4. Select Sensor Settings From the Menu
5. Select CH1 or CH2 from Sensor Settings
6. Select Next to Navigate to CH1 Alarm
7. Turn OFF or ON the Alarm FIG. 15 illustrates an exemplary process for customizing transmission intervals that includes the following steps (note: longer measure and transmit levels will result in improved/longer battery levels):

1. Wave device if inactive for 30 seconds or more
2. Selecting Settings Menu
3. Enter PIN to access the Settings Menu
4. Navigate to page 2 using the down button or page>button
5. Select Logging Settings
6. Use navigation buttons to select Transmit
7. Use navigation buttons to set desired Transmit Interval FIG. 16 illustrates an exemplary process for exporting settings to USB that includes the following steps:

1. Wave device if inactive for 30 seconds or more
2. Selecting Settings Menu
3. Select Export from Settings Menu
4. Select Export Settings
5. Select Next
6. Insert USB external storage device in the USB port and select Next
7. Mounting USB mass storage device
8. The device exports the following: alarm, channel, general, logging, network, network enterprise, TempTrack, PIN, Certificates
9. Unmounting the USB mass storage device
10. Finish—Settings have been exported FIG. 17 illustrates an exemplary process for importing settings from one device to another that includes the following steps:

1. Wave device if inactive for 30 seconds or more
2. Selecting Settings Menu
3. Select Setup Device from Settings Menu (on first power-up of the device)
4. Select USB
5. Select Next
6. Insert USB external storage device in the USB port and select Next
7. Mounting USB mass storage device
8. The device imports the following: alarm, channel, general, logging, network, network enterprise, TempTrack, PIN, Certificates
9. Setting have been successfully imported and applied 10a. If the Imported Settings do not include NPT server settings, user will be prompted to manually enter the date and time
10b. If Imported Settings include NPT server settings, the UTC date and time will be updated and displayed FIGS. 18 and 19 illustrate an exemplary process for registering devices in software that includes the following steps:

1. Choose Sensor Registration from Configuration tab on the left.
2. Input Sensor ID and Security ID, which may be found on the label on back of device.
3. Change Transmitter Type from Digital Temperature to a transmitter (e.g., either MX40 or MX50, etc.) listed on the transmitter type drop-down menu. The model number (e.g., MX40-WF or MX50-WF, etc.) is preferably listed on the label on the back of the unit.
4. Choose the channel and monitoring type from the drop-down menu. Select the property to be measured from the drop-down list.
5. Choose the appropriate group for the sensor to be associated with. It is preferable to add the sensor to a group. Depending on the user's view, the user may not be able to view or search for a sensor after it is registered depending what view is assigned to the user profile.
6. Repeat steps 1-5 on additional rows to add multiple sensors at once, or you can click the Add button in the bottom right corner to finish and add sensor(s).

Exemplary embodiments may be implemented for monitoring environmental conditions (e.g., temperature, humidity, carbon dioxide, oxygen, pressure, etc.) in a wide range of storage units, such as storage units for vaccines, medications, and other climate sensitive products in a hospital environment or other facility, etc. But aspects of the present disclosure should not be limited to only medical storage units in medical facilities. For example, exemplary embodiments of the environmental monitoring devices disclosed herein may be configured for monitoring of temperature and/or other environmental conditions in food service environments.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "includes," "including," "has," "have," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The term "about" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. For example, the terms "generally", "about", and "substantially" may be used herein to mean within manufacturing tolerances.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements, intended or stated uses, or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An environmental monitoring device for monitoring one or more environmental conditions, the device comprising:

a main printed circuit board (PCB) having a modular configuration including an expansion port/connector and capable of supporting a display module; and a short-range wireless communication interface disposed on the main PCB, the short-range wireless communication interface comprising a BLUETOOTH Low Energy (BLE) radio and being configured to establish a short-range wireless communication link with at least one other environmental monitoring device; and a plurality of different physically interchangeable communication modules implemented as daughter boards that are selectively connectible one-at-a-time with the expansion port/connector of the main PCB, each communication module implementing a different long-range wireless protocol;

wherein:

selective connection of a given one of the communication modules configures the device for wireless communication according to the corresponding long-range protocol;

the device includes an on-device user interface and is operable to initiate, via on-screen navigation, a serverless cloning operation in which a configuration dataset comprising one or more alarm thresholds, allowable ranges, logging and/or transmit intervals, and network settings is transmitted from the device to the at least one other environmental monitoring device over the BLE link and applied at the other environmental monitoring device without reliance on an external server; and the device is configured to sense, locally store, and report environmental data including at least temperature and/or humidity, and to generate a user-acknowledgeable alarm when a sensed condition is outside a user-defined allowable range.

2. The environmental monitoring device of claim 1, wherein the plurality of different communication modules comprises:

a Wi-Fi communication module for selectively configuring the environmental monitoring device for Wi-Fi communication when the Wi-Fi communication module is selectively connected with the expansion port/connector of the main PCB;

a cellular communication module for selectively configuring the environmental monitoring device for cellular communication when the cellular communication module is selectively connected with the expansion port/connector of the main PCB; and a 900 MHz communication module for selectively configuring the environmental monitoring device for 900 MHz communication when the 900 MHz communication module is selectively connected with the expansion port/connector of the main PCB.

3. The environmental monitoring device of claim 1, wherein the plurality of different communication modules comprises a plurality of expansion boards that are interchangeably connectible with the expansion port/connector of the main PCB thereby enabling the environmental monitoring device to accommodate the different wireless communication protocols associated with the plurality of expansion boards.

4. The environmental monitoring device of claim 1, further comprising a wireless communication interface for establishing a wireless communication link with a mobile device for enabling the mobile device to be useable over the wireless communication link for programming and/or configuring the environmental monitoring device.

5. The environmental monitoring device of claim 4, wherein:

the main PCB includes the wireless communication interface for establishing a wireless communication link with a mobile device; and/or the wireless communication interface comprises a BLUETOOTH radio for establishing a BLUETOOTH communication link with the mobile device for enabling the mobile device to be usable over the BLUETOOTH communication link for programming and/or configuring the environmental monitoring device.

6. The environmental monitoring device of claim 1, wherein:

the environmental monitoring device is a first environmental monitoring device; and the first environmental monitoring device comprises a wireless communication interface for establishing a wireless communication link with at least a second environmental monitoring device whereby the first environmental monitoring device is operable for initiating copying of the configuration of the first environmental monitoring device to the second environmental monitoring device via the wireless communication link.

7. The environmental monitoring device of claim 6, wherein:

the main PCB of the first environmental monitoring device includes the wireless communication interface for establishing a wireless communication link with at least the second environmental monitoring device; and/or the wireless communication interface of the first environmental monitoring devices comprises a BLUETOOTH radio for establishing a BLUETOOTH communication link with at least the second environmental monitoring device whereby the first environmental monitoring device is operable for initiating copying of the configuration of the first environmental monitoring device to the second environmental monitoring device via the BLUETOOTH communication link;

and/or the wireless communication interface of the first environmental monitoring device is operable for establishing a wireless communication link with a plurality of other environmental monitoring devices whereby the first environmental monitoring device is operable for initiating copying of the configuration of the first environmental monitoring device to the plurality of other environmental monitoring devices via the wireless communication link.

8. The environmental monitoring device of claim 1, wherein:

the environmental monitoring device comprises a housing defining an interior in which are positioned the main PCB, the display modules, and the wireless communication module that is selectively connected with the expansion port/connector of the main PCB; and the housing includes a button or other user input for silencing an alarm when the environmental monitoring device has detected that a monitored environmental condition has exceeded a threshold or is outside of an acceptable range.

9. The environmental monitoring device of claim 1, wherein the environmental monitoring device is configured for monitoring one or more environmental conditions of an environment including:

temperature of the environment;

humidity of the environment;

carbon dioxide level of the environment;

oxygen level of the environment; and/or pressure level of the environment.

10. The environmental monitoring device of claim 1, wherein:

the environmental monitoring device is configured for monitoring temperature of medication, drugs, and/or vaccines in a medical environment; or the environmental monitoring device is configured for monitoring temperature in a food service environment.

11. The environmental monitoring device of claim 1, wherein the main PCB supports a Liquid Crystal Display (LCD) interface through the display module for displaying sensed environmental conditions and/or parameters.

12. The environmental monitoring device of claim 1, wherein:

the environmental monitoring device is configured to be operable for configuring data by copying a given configuration from another environmental monitoring device; and/or the environmental monitoring device is configured to be operable such that a configuration process is triggered by on-screen navigation.

13. The environmental monitoring device of claim 1, wherein the environmental monitoring device is configured to meet Data Logger requirements found in Vaccine for Children program outlined by Centers for Disease Control and Prevention (CDC).

14. An environmental monitoring device for monitoring one or more environmental conditions, the device comprising a main printed circuit board (PCB) including an expansion connector to receive interchangeable long-range communication daughter boards and an on-board BLUETOOTH radio separate from the daughter boards, whereby the device is operable to:

establish a BLUETOOTH communication link with a plurality of other environmental monitoring devices; and trigger, via an on-screen configuration menu, server-less cloning of a configuration dataset from the device to the plurality of other environmental monitoring devices over BLUETOOTH, the configuration dataset including one or more alarm thresholds, allowable ranges, logging/transmit intervals, and network settings, wherein the cloning is performed without connection to an external server.

15. The environmental monitoring device of claim 14, wherein the BLUETOOTH radio is operable for establishing a BLUETOOTH communication link with a mobile device for enabling the mobile device to be usable over the BLUETOOTH communication link for programming and/or configuring the environmental monitoring device.

16. The environmental monitoring device of claim 14, wherein the environmental monitoring device is a first environmental monitoring device that comprises a BLUETOOTH radio for establishing a BLUETOOTH communication link with at least a second environmental monitoring device whereby the first environmental monitoring device is operable for initiating copying of the configuration of the first environmental monitoring device to the second environmental monitoring device via the BLUETOOTH communication link.

17. The environmental monitoring device of claim 14, wherein the environmental monitoring device is a first environmental monitoring device including a wireless communication interface operable for establishing a wireless communication link with a plurality of other environmental monitoring devices whereby the first environmental monitoring device is operable for initiating copying of the configuration of the first environmental monitoring device to the plurality of other environmental monitoring devices via the wireless communication link.

18. The environmental monitoring device of claim 14, wherein:

the main PCB has a modular configuration including an expansion port/connector and capable of supporting a display module; and the environmental monitoring device comprises a plurality of different communication modules interchangeably connectible with the expansion port/connector of the main PCB, whereby the environmental monitoring device is selectively configurable for wireless communication according to different wireless protocols depending on which of the different wireless communication modules is selectively connected with the expansion port/connector of the main PCB.

19. The environmental monitoring device of claim 18, wherein the plurality of different communication modules comprises:

a Wi-Fi communication module for selectively configuring the environmental monitoring device for Wi-Fi communication when the Wi-Fi communication module is selectively connected with the expansion port/connector of the main PCB;

a cellular communication module for selectively configuring the environmental monitoring device for cellular communication when the cellular communication module is selectively connected with the expansion port/connector of the main PCB; and a 900 MHz communication module for selectively configuring the environmental monitoring device for 900 MHz communication when the 900 MHz communication module is selectively connected with the expansion port/connector of the main PCB.

20. The environmental monitoring device of claim 18, wherein the plurality of different communication modules comprises a plurality of expansion boards that are interchangeably connectible with the expansion port/connector of the main PCB thereby enabling the environmental monitoring device to accommodate the different wireless communication protocols associated with the plurality of expansion boards.

21. The environmental monitoring device of claim 14, wherein:

the environmental monitoring device comprises a housing defining an interior in which are positioned the main PCB, the display modules, and the wireless communication module that is selectively connected with the expansion port/connector of the main PCB; and the housing includes a button or other user input for silencing an alarm when the environmental monitoring device has detected that a monitored environmental condition has exceeded a threshold or is outside of an acceptable range.

22. The environmental monitoring device of claim 14, wherein the environmental monitoring device is configured for monitoring one or more environmental conditions of an environment including:

temperature of the environment;

humidity of the environment;

carbon dioxide level of the environment;

oxygen level of the environment; and/or pressure level of the environment.

23. The environmental monitoring device of claim 14, wherein:

the environmental monitoring device is configured for monitoring temperature of medication, drugs, and/or vaccines in a medical environment; or the environmental monitoring device is configured for monitoring temperature in a food service environment.

24. The environmental monitoring device of claim 14, wherein the main PCB supports a Liquid Crystal Display (LCD) interface through the display module for displaying sensed environmental conditions and/or parameters.

25. The environmental monitoring device of claim 14, wherein:

the environmental monitoring device is configured to be operable for configuring data by copying a given configuration from another environmental monitoring device; and/or the environmental monitoring device is configured to be operable such that a configuration process is triggered by on-screen navigation.

26. The environmental monitoring device of claim 14, wherein the environmental monitoring device is configured to meet Data Logger requirements found in Vaccine for Children program outlined by Centers for Disease Control and Prevention (CDC).

* * * * *